United States Patent [19]

England

[11] 4,190,277

[45] Feb. 26, 1980

[54] DEVICE FOR INSERTION, MANIPULATION AND REMOVAL OF SOFT CONTACT LENSES

[76] Inventor: Robert C. England, P.O. Box 2829, 1024 Military Rd., Zanesville, Ohio 43701

[21] Appl. No.: 938,216

[22] Filed: Aug. 30, 1978

[51] Int. Cl.² .............................................. A61F 9/00
[52] U.S. Cl. ................................................ 294/1 CA
[58] Field of Search .................... 294/1 CA, 33, 99 R; 51/216 LP, 217 L; 81/43; 128/303 R, 321; 206/5.1; 351/160

[56] References Cited

U.S. PATENT DOCUMENTS

| 4,082,339 | 4/1978 | Ross | 294/1 CA |
| 4,126,345 | 11/1978 | List | 294/1 CA |

*Primary Examiner*—James B. Marbert
*Attorney, Agent, or Firm*—John Harrow Leonard

[57] ABSTRACT

A device having an elongated resilient body in the form of an open top trough with upwardly divergent side walls and open at the ends. One end of the body has integral lens gripping pads arranged one on each side wall. The pads are spaced from each other laterally of the body and are movable toward each other by flexure of the side walls. The pads are shaped so that, when they are engaged with a soft contact lens which is installed on the cornea of a human eye and then moved toward each other, they first flex the lens so that its posterior face disconforms to the cornea and air can enter therebeneath and release the adhesion of the lens to the cornea, and then support the lens by the device so that it can be removed from the eye by manipulation of the device. The opposite end of the body is arranged to support the lens in undistorted condition for insertion into the eye by manipulation of the device.

10 Claims, 9 Drawing Figures

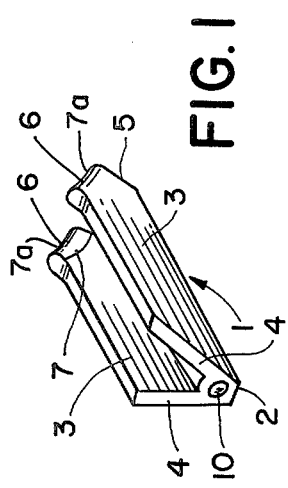
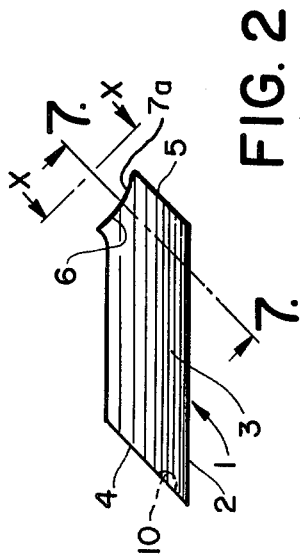
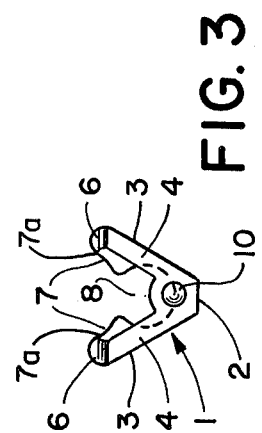
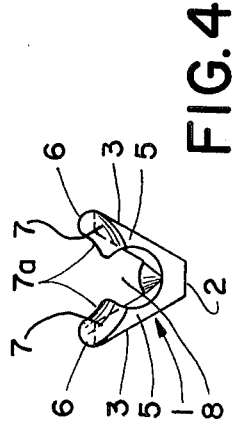
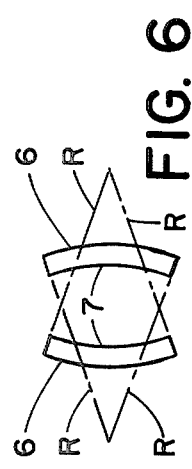
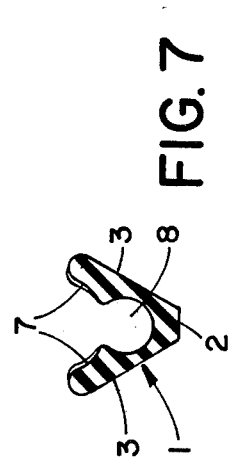
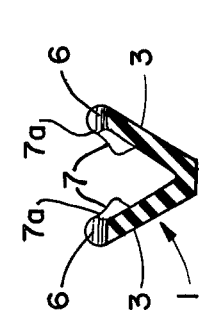
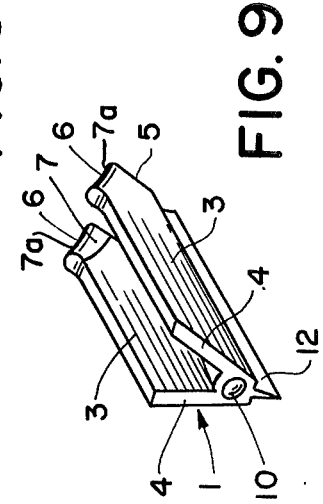
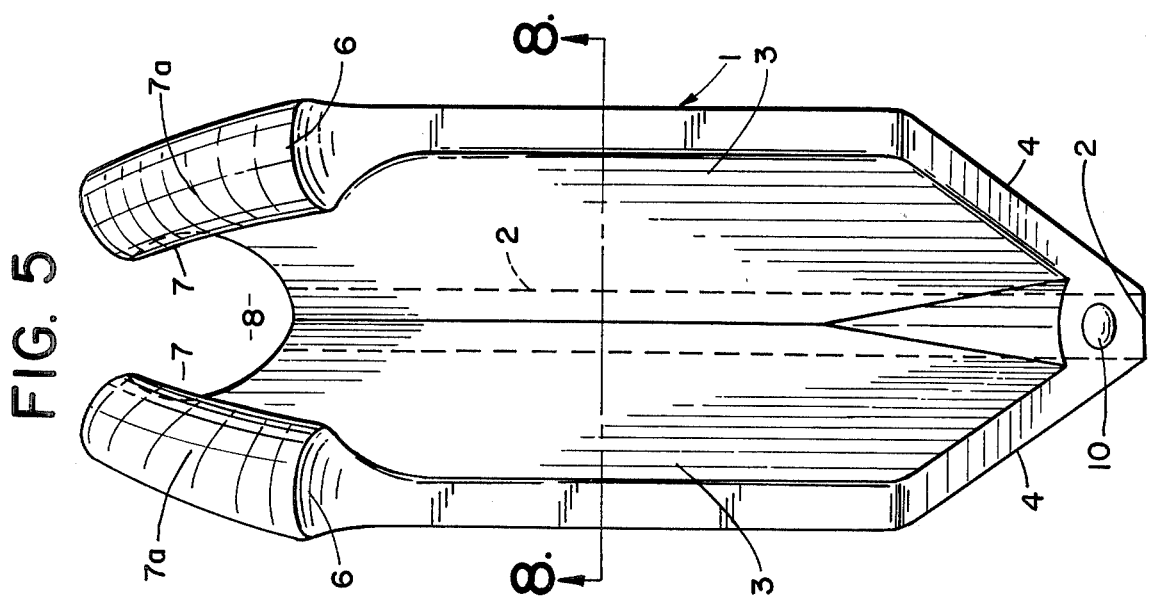

DEVICE FOR INSERTION, MANIPULATION AND REMOVAL OF SOFT CONTACT LENSES

BACKGROUND OF THE INVENTION (1) Field of Invention

Manually manipulatable device for inserting, holding, and removing soft contact lenses.

(2) Description of Prior Art

Suction cup types of devices for insertion, manipulation, and removal of hard contact lenses are known in the art. However, these prior devices are not functional with respect to soft contact lenses. Heretofore the soft lenses have been inserted in the eye by placing a properly prepared and wetted lens on the index finger and using the finger to move the lens into contact with the cornea, whereupon the lens adheres to the eyeball due partly to suction and partly to capillary attraction. Generally, the posterior face of the soft lens has a range of curvature which preferably approximates that of the cornea. The lens is very thin and pliable and, when applied to the cornea, tends to assume a shape in which the curvature of the posterior face is the same as that of the cornea. In doing so, the lens developes sufficient suction or capillary attraction to adhere sufficiently to the cornea so that it cannot be directly pulled off by pulling forces applied in a direction directly away from the eye parallel to the anterior-posterior axis of the lens. Such lenses cannot be removed by the conventional suction cups because the lens itself becomes, in effect, merely an extension or enlargement of the cup.

Presently such a soft contact lens is removed by slipping the lens by the finger in a direction laterally from its normal position on the cornea to an eccentric position, usually inferior-temporal to the cornea. Thereupon, due to the difference in radii of curvature of the posterior face of the lens and the sclera causes the lens to wrinkle or buckle, thereby allowing air to enter the space between the eye and lens. The entrant air breaks the adherence of the lens to the cornea, whereupon the lens can be pinched between the fingers sufficiently to release it entirely. This removal can be initiated only in the eccentric position of the lens, wherein the radii of the cornea and posterior face are different from each other.

Manipulation of the lens in preparation for insertion also is done by the fingers, with occasional inadvertent inversion or turning of the lens inside out. When such inversion occurs, the lens must be reverted before it can be installed, and such must be done very carefully to avoid damage to the lens surfaces and edges. Also, the fingers, especially the nails, may strike and damage the eye during insertion or removal of the lens, and infection from the fingers is an additional danger.

SUMMARY

The device of the present invention is designed to overcome these difficulties. It is composed of soft, resilient material, such as rubber, plastic, polyvinyl chloride, and the like, providing adequate rigidity and resiliency of respective portions where needed for functioning. The body carries integral pads of specialized shape and relation so that they can engage a soft contact lens on the eye, wrinkle or buckle the lens to relieve its suction and capillary attraction, and support it in said condition for removal from the eye by manipulation of the device.

Various objects and advantages of the invention will become apparent by reference to the following drawing and description disclosing a preferred embodiment of the invention.

BRIEF DESCRIPTION OF THE DRAWING

FIG. 1 is a perspective view of the device;

FIG. 2 is a side elevation of the device illustrated in FIG. 1;

FIG. 3 is a rear end elevation of the device viewed from the left in FIG. 2;

FIG. 4 is a front end elevation of the device, viewed from the right in FIG. 2;

FIG. 5 is an enlarged top plan view of the device;

FIG. 6 is a fragmentary plan view of the holding pads of the device, showing the curvature of their inner faces relative to an axis x—x extending endwise of, and parallel to the plane of, one of the pads;

FIG. 7 is a fragmentary cross sectional view of the pads of FIG. 6, taken on the line 7—7 of FIG. 2, showing the pads' curvature in a plane transversely of the axis x—x;

FIG. 8 is a cross sectional view taken on line 8—8 of FIG. 5; and

FIG. 9 is a view similar to FIG. 1, illustrating a modification of the device.

Referring to the drawing, the device comprises a unitary body 1, generally in the form of an open top, open end trough, having a narrow base portion 2 with sides 3 extending upwardly from the base 2 in divergent relation to each other. The rear edges 4 of the sides 3 are generally parallel to each other, as also are the front edges 5 of the sides 3, and the front edges 5 are parallel to the rear edges 4. All of these edges are inclined upwardly forwardly about 45° from the base 2, as best illustrated in FIG. 2.

The rear end of the body 1 is the lens insertion end and the front end of the body is the lens removal and manipulating end.

The front end carries a pair of laterally spaced holding pads 6 which, endwise of the pads, slope generally longitudinally of the sides at about 45° from the upper edges of the sides downwardly and forwardly of the body. The upper end of the front edges 5 meet the lower end of the pads 6 about half way between the base 2 and top of the body 1. The pads 6 preferably are integral with the side walls 3.

Each pad 6 has an inner face which is concavo-convex, being generally curvilinear and concave toward the inner face of the other pad, lengthwise of the pads, and thus each face presents toward the other a surface generally concave, as indicated at 7, with respect to a longitudinal median line between the associated pads, and parallel to a plane such as indicated at x—x. Each pad also is curvilinear upwardly endwise so as to be concave toward the plane x—x, as best indicated at 7a in FIG. 2. The jaws are slightly divergent from each other upwardly and rearwardly of the body from their lower ends, as best illustrated in FIGS. 4 and 5. Also, in cross section, as indicated in FIG. 7, the endwise and upwardly concave face 7 of each pad is curvilinear and convex toward the face of the other pad at all points along their lengths.

The general spacing of the pads from each other laterally of the body 1 may be varied to meet the size and specifications of the particular lens to be operated, if the lens varies greatly from the norm. As mentioned, the body 1 is open at both ends, as indicated at 8, to permit viewing in a mirror of the application of the ends of the body to the lens and the lens to the eye by the user of the lens when inserting or removing the lens.

At its rear end, distal to the pads 6, the body has a rearwardly open, shallow concavity 10 near the base 2 which provides an "insertion pad". The surface of the concavity 10 is in the form of a spherical segment having a radius approximately conforming to that of the anterior face of the lens with which it is to be used.

As mentioned, the plane of the rear end of the body, in which the open side of the concavity 10 lies, slopes at approximately 45° upwardly and forwardly of the device from the base 2, and the axis of the concavity, as is apparent in FIG. 2, is normal to this plane and hence is 45° to the longitudinal axis of the device.

Thus, in general, except for the pads themselves, all edges of the ends of the device are in planes parallel to each other, and the bottom or base 2 and the upper edges of the sides 3 are parallel to each other. Accordingly, in side elevation, the device appears generally as a parallelogram.

In cross section, the body 1 as a whole defines generally an isosceles trapezoid, the flattened base 2 being the smaller base, the sides 3 being the sides, and the plane of the open top, defined by the upper edges of the sides 3, being the larger base.

OPERATION

Removal of a lens is effected by applying the pads 6 firmly and evenly, but lightly, to the anterior surface of the lens while the lens is centered on the cornea, then, while so applied, squeezing the sides 3 laterally toward each other to move the pads toward each other while they remain in contact with the lens. Due to the convex cross section and lengthwise concaveness of the pad faces, as described, the pads have substantially line contact with the lens surface throughout their length, and without any sharp edges in engagement with the lens. This type of engagement and movement causes portions of the lens between the pads to form initially and temporarily into one or more slightly rounded undulations which, endwise, extend generally endwise of the pads. Each of these undulations admits ambient air into the space it forms between the lens and cornea, and this entrant air breaks the suction and capillary adhesion, and spreads readily throughout the space between the lens and cornea as the lens is pulled forwardly by the body while the lens is thus held between the pads. Thereby, the lens can readily be supported by the pads when the lens is thus removed, and deposited in a suitable receptacle.

The convexity of the pad faces, in the cross section of the pads, allows a progressive movement of the portion of the lens between the pads into the contracting space between the approaching pads so that the lens tends gradually to fold upon itself to form one large undulation which, lengthwise, extends generally endwise of pads and which, in cross section, opens toward the cornea. The adjacent portions of the lens do not become so tightly pressed toward each other as to transform the undulations into tight folds which would cause the adjacent portions to adhere to each other in folded condition.

The lens is inserted simply by seating its anterior face in the cavity 10, preferably with that face wetted or moistened so that it adheres lightly to the cavity wall. It is then applied centrically to the cornea by moving the body endwise toward the eye while aligned with its required centered final position on the cornea.

ADVANTAGES

The lens is not required to be moved to eccentric position relative to the cornea preparatory to insertion or removal.

The wearer is able to peer endwise through the device into a mirrow for monitoring his operations, whereas the prior method, due to its requirements of installing the lens in eccentric relation, or its movement to eccentric relation for removal, necessitated that the wearer look upwardly and away from a normal straight forward line of sight, which made viewing in a mirror difficult.

The lens is handled by soft pads rather than rough finger tips and finger nails, thus protecting both the lens and the eye of the wearer.

Such lenses are easily contaminated, and use of the device eliminates this danger of contamination that might occur if the lens were handled by the fingers.

Insertion of the lens is effected by placing it in the concavity 10 where, being wet, it is held by capillarity. A portion of the lens protrudes above the concavity and can be looked through into a mirror to monitor the inserting operation. This can be done after the lens is wetted with the usual saline rinsing fluid and without touching it with the fingers.

The lens can be inspected by holding it up to the light with the device, without touching it with the fingers, while it is held in the concavity.

Upon contact with the cornea, the lens drapes over the cornea and is attracted thereto sufficiently so that slow retraction of the body will detach the device from the lens while leaving the lens in place on the cornea.

The rear end of the body can be provided with an adapter to hold a small disposable flashlight for illuminating the ocular area during lens removal.

If desired, the modified form of the device, illustrated in FIG. 9, may be employed. The modified device of FIG. 9 is the same in all respects as that disclosed in FIGS. 1 through 8, except that a ventral fin 12 is provided and depends from the underside of the base 2 and extends substantially the entire length of the base 2. The ventral fin 12 is for ease in handling, the fin being, in effect, merely a handle.

Having thus described my invention, I claim:

1. A device for inserting and removing a soft contact lens from the eye of a wearer, and comprising a body adapted to be held in the hand and moved thereby universally relative to the eye;

a pair of lens engaging elongated pads carried by the body in spaced relation to each other transversely of their lengths;

said pads having elongated lens engaging faces, respectively;

said faces being curvilinear and concave toward each other in longitudinal section and being curvilinear and convex toward each other in cross section, and, in the normal spaced position of the pads being engageable with the anterior face of a soft contact lens in the form of a spheroidal segment at locations thereon inwardly from the edges of the lens and spaced apart transversely of the lens, while the lens is installed on the eye, said pads being movable toward each other by portions of the hand, while said faces are so engaged with the installed lens, to cause said faces to flex the lens out of its normal spheroidal contour in a manner to admit air between the rear face of the lens and the eye on which it is installed, and to hold the lens in flexed condition while it is on the eye and during its removal from the eye by movement of the body away from the eye.

2. A device according to claim 1 wherein said faces of the pads are divergent from each other in one direction lengthwise of the faces for applying said flexing forces to the lens inwardly laterally of the lens, and thereby to cause progressive movement of the portion of the lens between said lens engaging faces into the contracting space between the pads, and to cause progressive non-uniform breakage of the adhesive forces which keep the lens in place on the eye.

3. A device according to claim 1 wherein said faces of the pads face partially outwardly of the body and, in the direction of their length, extend generally parallel to a common plane which in one cross dimension of the body is normal to the length of the body and, in the cross dimension of the body at a right angle to said one cross dimension, is oblique to the length of said body.

4. A device according to claim 3 wherein the angle of obliquity is about 45°.

5. A device according to claim 1 wherein said body is elongated and has a front end and a rear end, said lens engaging pads are at its front end; at its rear end said body has a shallow lens engaging concavity which opens rearwardly of the body and of which the rear face is generally in the shape of the surface of a spherical segment for engaging the forward face of the lens.

6. A device according to claim 1 wherein said entire device is a one piece molded unitary structure of soft, resilient, self-restoring elastomeric material.

7. A device according to claim 1 wherein each of said concavo-convex faces is also concave outwardly from the body in a longitudinal section at a right angle to the longitudinal sections in which the faces are concave toward each other.

8. A device according to claim 1 wherein the body normally holds the pads in their said laterally spaced relation in which the spacing of said lens engaging faces is less than the distance between opposite edges of the lens.

9. A device for inserting and removing a soft contact lens from the eye of a wearer, and comprising a body adapted to be held in the hand and moved thereby universally relative to the eye;

a pair of lens engaging elongated pads carried by the body in spaced relation to each other transversely of their lengths;

said pads being engageable with the anterior face of a soft contact lens in the form of a spheroidal segment at locations thereon inwardly from the edges of the lens and spaced apart transversely of the lens, while the lens is installed on the eye; said pads being movable toward each other by portions of the hand, while said faces are so engaged with the installed lens, to cause said faces to flex the lens out of its normal spheroidal contour in a manner to admit air between the rear face of the lens and the eye on which it is installed, and to hold the lens in flexed condition while it is on the eye and during its removal from the eye by movement of the body away from the eye;

said body being in the form of a trough having front and rear ends, a base portion extending from front to rear, and said trough being open at the top throughout its length, and being open at its ends, and having side walls extending upwardly from said base portion in divergent relation relative to each other;

said side walls are resilient so that they can be flexed toward each other by the hand holding the body; and said pads are carried on said side walls, respectively, adjacent the forward end of the body.

10. A device according to claim 9 wherein said forward ends of the side walls slope upwardly forwardly from said base portion partway of their lengths to an intermediate location, and then slope upwardly, rearwardly of the body from said intermediate location; and said pads are on the upwardly rearwardly sloping portions of the side walls, respectively.

* * * * *